(12) United States Patent
Kurihara et al.

(10) Patent No.: US 12,194,152 B2
(45) Date of Patent: Jan. 14, 2025

(54) SHELL COMPOSITION AND CAPSULE USING THE SHELL COMPOSITION

(71) Applicants: SUNSHO PHARMACEUTICAL CO., LTD., Fuji (JP); MP Gokyo Food & Chemical Co., Ltd., Osaka (JP)

(72) Inventors: Shinya Kurihara, Fujinomiya Shizuoka (JP); Makoto Miwa, Fujinomiya Shizuoka (JP); Tomokazu Okayama, Fujinomiya Shizuoka (JP); Keiichi Kubota, Fujinomiya Shizuoka (JP); Takanori Kobayashi, Fujinomiya Shizuoka (JP); Rei Iwata, Chuo Tokyo (JP); Kenta Yamanishi, Toyonaka Osaka (JP)

(73) Assignees: Sunsho Pharmaceutical Co., Ltd., Fuji (JP); MP Gokyo Food & Chemical Co., Ltd., Osaka (JP)

( * ) Notice: Subject to any disclaimer, the term of this patent is extended or adjusted under 35 U.S.C. 154(b) by 1009 days.

(21) Appl. No.: 16/975,643

(22) PCT Filed: Feb. 26, 2019

(86) PCT No.: PCT/JP2019/007278
§ 371 (c)(1),
(2) Date: Aug. 25, 2020

(87) PCT Pub. No.: WO2019/167934
PCT Pub. Date: Sep. 6, 2019

(65) Prior Publication Data
US 2020/0405647 A1    Dec. 31, 2020

(30) Foreign Application Priority Data

Feb. 28, 2018  (JP) ................ 2018-034621

(51) Int. Cl.
| | | |
|---|---|---|
| A61K 9/48 | (2006.01) |
| A23L 29/219 | (2016.01) |
| A23L 29/238 | (2016.01) |
| A23L 29/269 | (2016.01) |
| A23P 10/30 | (2016.01) |

(52) U.S. Cl.
CPC .......... *A61K 9/4816* (2013.01); *A23L 29/219* (2016.08); *A23L 29/238* (2016.08); *A23L 29/27* (2016.08); *A23P 10/30* (2016.08); *A23V 2002/00* (2013.01)

(58) Field of Classification Search
CPC .................................................. A61K 9/4816
See application file for complete search history.

(56) References Cited

U.S. PATENT DOCUMENTS

| | | |
|---|---|---|
| 10,898,438 B2 | 1/2021 | Baruzzi et al. |
| 2005/0069579 A1 | 3/2005 | Kamaguchi et al. |
| 2008/0248102 A1 | 10/2008 | Rajewski et al. |
| 2011/0217249 A1 | 9/2011 | Dreher |
| 2011/0319503 A1* | 12/2011 | Muller ............ B29C 43/44 514/778 |
| 2013/0302309 A1 | 11/2013 | Yang |
| 2015/0335586 A1 | 11/2015 | Baruzzi et al. |
| 2016/0000740 A1 | 1/2016 | Zhang et al. |
| 2016/0021927 A1 | 1/2016 | Kondo |

FOREIGN PATENT DOCUMENTS

| | | |
|---|---|---|
| CN | 103877586 A | 6/2014 |
| CN | 106109438 A | 11/2016 |
| CN | 106214660 A | 12/2016 |
| EP | 1447082 A1 | 8/2004 |
| EP | 2700415 A2 | 2/2014 |
| EP | 2865375 A1 | 4/2015 |
| EP | 3141129 A1 | 3/2017 |
| EP | 3785707 A1 | 3/2021 |
| JP | H07-196478 A | 8/1995 |
| JP | H11-253112 A | 9/1999 |
| JP | 2000202003 A * | 7/2000 |
| JP | 2003-093017 A | 4/2003 |
| JP | 2006-299052 A | 11/2006 |
| JP | 2007-176886 A | 7/2007 |
| JP | 4242266 B2 | 3/2009 |
| JP | 2009-102293 A | 5/2009 |
| JP | 2009-173607 A | 8/2009 |
| JP | 4500000 B2 | 7/2010 |
| JP | 2013-537902 A | 10/2013 |

(Continued)

OTHER PUBLICATIONS

Maria Aparecida Vieira Teixeira Garcia, Cleverson Fernando Garcia, and André Augusto Gomes Faraco. "Pharmaceutical and Biomedical Applications of Native and Modified Starch: A Review." Starch—Starke vol. 72, 2020, Article 1900270, pp. 1-15. (Year: 2020).*

English Translation of JP 2000-202003 A. Obtained by examiner on Sep. 29, 2023. Originally published in Japanese in 2000, 6 printed pages. (Year: 2000).*

Ha Lieberman, L Lachman, and JB Schwartz. "Pharmaceutical Dosage Forms: Tablets vol. 1, Second Edition Revised and Expanded." Marcel Dekker Inc., 1989, pp. i-xviv, 1-593 and two additional pages (610 total sheets). (Year: 1989).*

L Hadisoewignyo and A Fudholi. "Role of Natural Polysaccharides Xanthan Gum-Locust Bean Gum in Per-Oral Drug Delivery Systems." Proceeding International Conference and Talk Show on Medicinal Plant, Jakarta Oct. 19-21, 2010, pp. 246-252. (Year: 2010).*

Zhan, D.F. et al., "Xanthan-locust bean gum interactions and gelation", Carbohydrate Polymers, 1993, vol. 21, Issue 1, pp. 53-58.

(Continued)

*Primary Examiner* — Isaac Shomer
(74) *Attorney, Agent, or Firm* — Kim & Stewart LLP

(57) ABSTRACT

Provided is a shell composition that is formed with a water-insoluble powder such as starch and/or a water-soluble polymer such as dextrin as a base component, and with locust bean gum and/or xanthan gum as a gelling agent. This shell composition enables a novel shell composition which can favorably form a shell without using carrageenan, has favorable properties that enable the shell composition to substitute traditional shells that use a gelatin shell or carrageenan, and comprises a plant-derived base.

12 Claims, No Drawings

(56) References Cited

FOREIGN PATENT DOCUMENTS

| JP | 5539621 B2 | 7/2014 | |
|---|---|---|---|
| TW | 201622708 A | 7/2016 | |
| WO | 00/18835 A1 | 4/2000 | |
| WO | 01/03677 A1 | 1/2001 | |
| WO | 03/043609 A1 | 5/2003 | |
| WO | 2014/152098 A1 | 9/2014 | |
| WO | 2017/022230 A1 | 2/2017 | |
| WO | WO-2017042295 A1 * | 3/2017 | ............. A21D 2/186 |

OTHER PUBLICATIONS

Notice of Reasons for Refusal mailed Mar. 28, 2023 in corresponding Japanese Patent Application No. 2020-503518, with English translation, 10 pages.

Joanne K. Tobacman, "Review of Harmful Gastrointestinal Effects of Carrageenan in Animal Experiments" Environmental Health Perspectives, Oct. 2001, vol. 109, No. 10, pp. 983-994.

Sumit Bhattacharyya et al., Exposure to Common Food Additive Carrageenan Alone Leads to Fasting Hyperglycemia and in Combination with High Fat Diet Exacerbates Glucose Intolerance and Hyperlipidemia without Effect on Weight, Journal of Diabetes Research, Mar. 2015, 13 pages.

English Translation of International Search Report dated Sep. 6, 2019, mailed in counterpart International Application No. PCT/JP2019/007278, 2 pages.

* cited by examiner

SHELL COMPOSITION AND CAPSULE USING THE SHELL COMPOSITION

TECHNICAL FIELD

The present invention relates to a shell composition which can be prepared without need to use gelatin or carrageenan, and a capsule preparation in which a drug or food is encapsulated in a capsule formed from the shell composition.

BACKGROUND ART

Heretofore, capsules prepared using gelatin as a base material have been widely used as capsules for drugs, health foods and the like. However, for reasons such as religious restrictions, concerns about allergy, and increasing concerns about safety, there is a tendency to avoid the use of an animal-derived raw material such as gelatin. To address this issue, a capsule shell using a plant-derived raw material, e.g., starch, as a base material has been proposed in recent years.

As a capsule shell using a plant-derived component as a base material as mentioned above, a capsule shell is proposed, for example, in which starch or a starch decomposition product, e.g., dextrin, or a mixture thereof is used as a base material and carrageenan is used as a gelling agent (JP 4242266 B2, JP 5539621 B2). Also proposed is a capsule shell, in which two types of galactans having different molecular weights or different anhydrogalactose contents are mixed together and guar gum or a starch decomposition product is further added to the mixture, wherein carrageenan is employed as an example of galactan (JP 4500000 B2).

In recent years, however, regarding carrageenan, which has been added to these capsule shell compositions, the demand therefor has increased in the world, and there is concern a drain on resources, an insufficient supply of a gelling agent, and rising resource prices. For that reason, development of a capsule shell using a plant-derived gelling agent other than carrageenan is in demand.

PRIOR ART DOCUMENTS

Patent Documents

Patent Document 1: JP 4242266 B2
Patent Document 2: JP 5539621 B2
Patent Document 3: JP 4500000 B2

SUMMARY OF INVENTION

Technical Problem

The present invention has been accomplished in these situations, and aims to provide a novel shell composition which is formed with a plant-derived base material, can be formed into a film without need to use carrageenan, has good performance for use as a substitute capsule shell for a conventional shell prepared using a gelatin film or carrageenan.

Solution to Problem

The present inventors have made extensive and intensive studies for the purpose of achieving the above-described object. As a result, it is found that, when a plant-derived water-insoluble powder, e.g., starch, and a plant-derived water-soluble polymer, e.g., a starch decomposition product, are used as base materials and are gelatinized using locust bean gum or xanthane gum, it becomes possible to produce a shell having capsule shapability, cracking performance, strength, transparency, adhesiveness and gas barrier properties at levels required for satisfactory use as a capsule shell. This finding leads to the accomplishment of the present invention.

Thus, the present invention provides a shell composition and a capsule preparation as described below.

1. A shell composition formed with a plant-derived water-insoluble powder and/or a plant-derived water-soluble polymer as a base material component and locust bean gum and/or xanthane gum as a gelling agent.
2. The shell composition according to the above item 1, wherein the water-insoluble powder is starch.
3. The shell composition according to the above item 2, wherein the starch is distarch phosphate and/or heat-moisture-treated starch.
4. The shell composition according to the above item 3, wherein the distarch phosphate is etherified distarch phosphate and/or esterified distarch phosphate.
5. The shell composition according to the above item 4, wherein hydroxypropyl distarch phosphate is included as the etherified distarch phosphate.
6. The shell composition according to any one of the above items 1 to 5, wherein the water-soluble polymer is a starch decomposition product and/or polydextrose.
7. The shell composition according to the above item 6, wherein the starch decomposition product is indigestible dextrin.
8. The shell composition according to any one of the above items 1 to 7, wherein the water-insoluble powder and the water-soluble polymer are contained as the base material components at a ratio of 1/99 to 99/1 by weight.
9. The shell composition according to any one of the above items 1 to 8, wherein the locust bean gum and the xanthane gum are contained as the gelling agents at a ratio of 90/10 to 10/90 by weight.
10. The shell composition according to any one of the above items 1 to 9, wherein the gelling agent is contained in an amount of 0.1 to 80 parts by weight relative to 100 parts by weight of the base material component.
11. A capsule preparation comprising a drug or food encapsulated in a hard capsule or a soft capsule each comprising the shell composition according to any one of the above items 1 to 10.

Advantageous Effects of Invention

According to the present invention, there can be provided a shell composition which can be prepared without adding gelatin or carrageenan and can become a substituent for conventional capsule shells prepared using gelatin or carrageenan, and a capsule preparation produced using the shell composition.

DESCRIPTION OF EMBODIMENTS

Hereinbelow, the present invention is described in detail.
The shell composition of the present invention is formed with a plant-derived water-insoluble powder and/or a plant-derived water-soluble polymer as a base material and also with locust bean gum and/or xanthane gum as a gelling agent. In the present invention, as said plant-derived water-insoluble powder and plant-derived water-soluble polymer, an edible products may be used preferably. In this case, "edible" means to be pharmaceutically acceptable when applied to medical use, or to be sanitationaly acceptable when applied to food use. In the present disclosure, the "shell" may be referred to as a coating. In the present disclosure, a "plant-derived" material is referred to as a non-animal-derived material, and may include an algae-derived material. In an embodiment, the coating composition of the present invention includes no or a negligible amount of animal-derived material. In an embodiment, the coating composition of the present invention includes no or a negligible amount of carrageenan.

The water-insoluble powder is not particularly limited, and starch is used preferably, and heat-moisture-treated starch, high-amylose starch, heat-moisture-treated high-amylose starch, and heat-moisture-treated high-amylose cornstarch are used particularly preferably, and a mixture thereof may also be used.

As the starch, distarch may be used, and distarch phosphate, etherified distarch phosphate, and esterified distarch phosphate can be used preferably. In this case, hydroxypylation is exemplified as the etherification, and acetylation is exemplified as the esterification.

Examples of the water-insoluble powder other than starch include cellulose and agar.

The particle diameter of the water-insoluble powder is not particularly limited, and is preferably a 30-mesh JIS standard sieve (JIS Z 8801-1) or less, particularly preferably a 60-mesh JIS standard sieve or less. If the particle diameter is larger than a 30-mesh sieve, the dispersibility of the water-insoluble powder in a liquid may become low and a satisfactory level of film strength may not be achieved. It is acceptable for the water-insoluble powder to contain a trace amount of a soluble solid matter. More concretely, the water-insoluble powder having a soluble solid matter content of 10% by weight or less, preferably 5% by weight or less, can be used without difficulty.

As the water-soluble polymer, a starch decomposition product or polysaccharides such as polydextrose and cellulose can be used. A starch decomposition product can be used preferably, and indigestible dextrin can be used particularly preferably. In this case, a hydrogenated (reduced) starch decomposition product, particularly hydrogenated (reduced) indigestible dextrin, can be used preferably.

The molecular weight of the water-soluble polymer is not particularly limited, and it is preferred for the water-soluble polymer to have a number average molecular weight of 1,000 to 100,000, particularly preferably 1,000 to 50,000. If the number average molecular weight is less than 1,000, a highly sticky shell may be formed, resulting in such a disadvantage that capsules using the shell may be more likely to be adhered to each other. If the number average molecular weight is more than 100,000, the shell composition may be less likely to be gelatinized.

As the base material to be used in the shell composition of the present invention, the water-insoluble powder or the water-soluble polymer may be used singly. In particular, from the viewpoint of strength and a heat-sealing property of a wet shell and elasticity and adhesiveness of a capsule produced by drying the wet shell, it is preferred to use the water-insoluble powder and the water-soluble polymer in combination. In this case, the ratio of the amount of the water-insoluble powder to the amount of the water-soluble polymer is not particularly limited, and the (water-insoluble powder)/(water-soluble polymer) ratio is preferably 1/99 to 99/1, particularly preferably 20/80 to 70/30. If the amount of the water-insoluble powder is too much, the shaping of the shell becomes difficult and the strength and heat-sealing property of the wet shell may be degraded. If the amount of the water-soluble polymer is too much, the wet shell may become sticky and a capsule produced by drying the wet shell may be deteriorated in crack resistance, or may become sticky and therefore may be degraded in blocking properties.

Next, locust bean gum that can be used as the gelling agent is a polysaccharide in which β-D-mannose molecules are bonded with a β-1,4 bond to form the main chain and an α-D-galactose molecule is bonded with an α-1,6 bond to form a side chain. The type of locust bean gum is not particularly limited, and locust bean gum in which the content ratio of mannose to galactose is about 4:1 can be used for example.

Xanthane gum that can be used as the gelling agent is a natural gummy substance produced by fermenting glucose or the like by a microorganism, *Xanthomonas campestris*, to accumulate a polysaccharide in the outside of the microorganism cell body and then purifying and grinding the polysaccharide. As the xanthane gum of this type, a commercially available produce can be used, such as Echo Gum® (manufactured by DSP GOKYO FOOD & CHEMICAL Co., Ltd.), Monat Gum® (manufactured by DSP GOKYO FOOD & CHEMICAL Co., Ltd.) and Rhaball Gum® (manufactured by DSP GOKYO FOOD & CHEMICAL Co., Ltd.).

As the gelling agent to be used in the shell composition of the present invention, the locust bean gum or the xanthane gum may be used singly or in combination depending on the intended use or the purpose of the use. For example, in the case where it is intended to produce a soft capsule, a combination of these gums is preferably used, wherein the ratio of the amount of the locust bean gum to the amount of the xanthane gum is not particularly limited and is preferably (locust bean gum)/(xanthane gum)=90/10 to 10/90 by weight, particularly preferably 70/30 to 20/80 by weight. If the amount of the locust bean gum is too much, the thickening effect may be increased and therefore stickiness may increase. If the amount of the xanthane gum is too much, the fluidability of a shell solution may become poor and a shell formed from the solution may become brittle. In the case where it is intended to produce a seamless capsule, although a combination of the locust bean gum and the xanthane gum can be used, it is enough to use either one of the locust bean gum and the xanthane gum for the formation of a shell having satisfactory performance.

The amount of the gelling agent to be added may be adjusted appropriately depending on the strength, hardness, flexibility, shape, thickness or the like required for the shell, and is not particularly limited. In particular, the amount is preferably 80 parts by weight or less, particularly preferably 50 parts by weight or less, still more preferably 30 parts by weight or less, relative to 100 parts by weight of the base material component. In this case, if the amount of the gelling agent added is less than 0.01 parts by weight, a wet shell may be degraded in strength and heat-sealing property and may become sticky and a capsule produced after drying the wet shell may often undergo blocking or cracking. The lower limit of the amount of the gelling agent to be added is not particularly limited, and is preferably 0.1 parts by weight or more, particularly preferably 0.1 parts by weight or more. If the amount of the gelling agent added is more than 80 parts by weight, the fluidability of a shell solution may decrease and consequently a shell may not be formed properly.

In the shell composition of the present invention, it is possible to add a plasticizer to modulate the elasticity or the like of the composition, if necessary. Examples of the plasticizer include glycerin, sorbitol, maltitol, and ethylene glycol. These plasticizers may be used singly or a combination of two or more of them may be used. Among these compounds, glycerin is preferably used. The amount of the plasticizer to be added may be adjusted appropriately depending on the intended use, and is not particularly limited. The amount is preferably 0.1 to 80 parts by weight, particularly preferably 20 to 60 parts by weight, relative to 100 parts by weight of the base material component.

In the shell composition of the present invention, in addition to the base material component, the gelling agent, and the plasticizer, it is possible to add pullulan, agar or the like for the purpose of, for example, modulating the hardness of the capsule.

In the shell composition of the present invention, it is also possible to add a known additive as required without departing from the object of the present invention. For example, a coloring agent, a flavoring agent, a sweetening gent, a preservative agent, a fragrance or the like may be added in an appropriate amount.

The shell composition of the present invention may be shaped into, for example, a hard capsule or a soft capsule, and a drug or food may be encapsulated in the capsule to produce a capsule preparation. Alternatively, the shell composition may be formed into a coating film for coating the surface of a drug or food which is shaped into a tablet or granules. In particular, the shell composition can be used preferably as a shell composition for forming a soft capsule. In the present disclosure, "drug" and "food" are used in accordance with the definitions provided by the Federal Food, Drug, and Cosmetic Act. In an embodiment, the drug and food may be examples of an orally-administrable article.

In this case, as the method for forming the shell composition of the present invention into a capsule or a coating film, a known method or a known production apparatus may be employed without modifications. For example, in the case where it is intended to produce a soft capsule by a known rotary die method, the production can be performed in the following manner.

Firstly, respective components of the shell composition of the present invention is suspended in water, the resultant solution is dissolved by warming to produce a shell solution, and then the shell solution is maintained at a temperature equal to or higher than a gelation temperature. Subsequently, the shell solution is spread on a smooth metal plate, and is then cooled and gelatinized to produce a wet shell film. Two of the wet shell films are set in such a manner that the wet shell films are overlapped on each other at a contact point between two rotating molds, then a content, which is extruded in a certain amount by means of a pump and drops vertically from the pump, is wrapped with the two wet shell films, and then the resultant product is compressed or heat-sealed and then punched out to produce a wet capsule. The wet capsule is dried to produce a soft capsule.

Alternatively to the rotary die method, a known double nozzle method (seamless method) may also be employed. In either method, the process be carried out by a known procedure. The details about the methods are described in, for example, "Manufacture technology for solid tablet" (Yusaku Shoji, first published on Mar. 5, 1985, CMC publishing Co., Ltd.).

EXAMPLES

The present invention is described in more detail with reference to Examples. However, the present invention is not intended to be limited by these Examples.

Examples

The components were suspended in water in the amounts shown in each of Tables 1 to 5, and the resultant suspension was dissolved by warming at 90° C. or higher for 2 hours to prepare a shell solution. The shell solution was spread on a smooth metal plate, and was then cooled to gelatinize the shell solution, thereby producing a wet shell film (thickness: 1.0 mm). Subsequently, a elliptic-sphere shaped wet capsule was produced using a medium-chain fatty acid triglyceride (MCT) as a content and using a rotary die-type capsule filling machine, and the wet capsule was dried in a drying machine that was set to 40±2° C. and less than 20% RH (relative humidity) to produce a soft capsule preparation. The soft capsule preparation was produced so that the water content in the capsule shell composition after drying became 10±1% by weight.

With respect to each of the soft capsules and the capsule shell films thereof thus produced, the state of the wet shell film was evaluated by the following methods. With respect to sample Nos. 26 to 30, 41 to 45, and 56 to 65, the appearance and physical properties of the capsule were also evaluated by the methods shown below. The results are shown in Tables 1 to 4.

[State 1 (Stickiness) of Wet Shell Film]

A sample prepared by placing each of the shell solutions on a petri dish to form a film was dried at a room temperature for 24 hours, and the stickiness of the film (50 mm×50 mm) was evaluated in accordance with the following manner. A metal plate having a weight of 100 g was put on the film, and then was lifted up from the film at 60 seconds later, the stickiness was evaluated from an adhesiveness at this time in accordance with the following criteria.

⊚: the film peeled off from the metal plate in less than 30 seconds;

○: the film peeled off from the metal plate in 30 to 60 seconds;

Δ: the film peeled off from the metal plate after more than 60 seconds; and

X: the film did not peeled off from the metal plate.

[State 2 (Heat-Sealing Property) of Wet Shell Film]

A sample that was formed into a film was bonded with a heat sealer at 80 to 90° C., and the resultant product was strained from both ends with hands to evaluate the heat-sealing property (peel strength) in accordance with the following criteria:

⊚: good (the film did not peeled off, even though it was pulled strongly);

○: moderate (the film did not peeled off, even though it was pulled);

Δ: weak (the film gradually peeled off, when it was pulled); and

X: detached easily (the film peeled off easily only by pinching).

[Appearance of Capsule]

The produced capsules were examined with naked eyes to determine the four items of color, shape, presence of scratches, and surface smoothness thereof. If any one of those items failed, it was determined to be defective products; and the appearance of capsule was evaluated on the basis of the percentage of the number of acceptable products having no problems (whole number: about 5,000 capsules) in accordance with the following criteria:

⊚: 99.7% or more;
○: 95% or more;
Δ: 68% or more; and
X: 67% or less.

[Physical Property 1 (Adhesiveness) of Capsule]

Twenty capsules were placed in a No. 6 glass sample bottle and were then stored in a thermostat bath at 40° C. and 75% RH for 48 hours while being opened. The moisture-absorbing capsules were evaluated with respect to the adhesiveness between capsules by the following method. An impact was applied to the sample bottle in which the capsules were contained, and it was examined whether or not the capsules fell apart. The adhesiveness was evaluated in accordance with the following criteria:

⊚: capsules fell apart only by putting the bottle upside down;
○: capsules fell apart when the bottle was put upside down and then dropped from a height of 2 cm on a table; and
Δ: capsules fell apart when the bottle was put upside down and then dropped from a height of 4 cm on a table.

[Physical Property 2 (Hardness) of Capsule]

The finished capsules were dried under reduced pressure (700 mmHg) in a desiccator, and the breaking hardness (kg) of the capsule was measured with a Monsanto hardness tester (maximum hardness: 30 kg or more) and was evaluated in accordance with the following criteria. In the following criteria, when the rating was ○ (15 kg or more), it was determined that the hardness was acceptable for commercial distribution.

⊚: 30 kg or more;
○: less than 30 kg and 15 kg or more;
Δ: less than 15 kg and 5 kg or more; and
X: less than 5 kg.

TABLE 1

| | | Sample No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| Compounding (part(s) by weight) | Base material | Hydroxypropylated distarch phosphate | | | 1 | | | | | 0.5 | | | | | 0 | | |
| | | Heat-moisture-treated starch | | | 0 | | | | | 0.5 | | | | | 1 | | |
| | | Indigestible dextrin | | | 99 | | | | | 99 | | | | | 99 | | |
| | Gelling agent | Locust bean gum | 2 | 4 | 10 | 14 | 18 | 2 | 4 | 10 | 14 | 18 | 2 | 4 | 10 | 14 | 18 |
| | | Xanthane gum | 18 | 16 | 10 | 6 | 2 | 18 | 16 | 10 | 6 | 2 | 18 | 16 | 10 | 6 | 2 |
| | Plasticizer | Glycerin | | | 30 | | | | | 30 | | | | | 30 | | |
| | Water | | | | 200 | | | | | 200 | | | | | 200 | | |
| Evaluation | State 1 (stickiness) of wet shell film | | ○ | ○ | ○ | Δ | Δ | ○ | ○ | ○ | Δ | Δ | ○ | ○ | ○ | Δ | Δ |
| | State 2 (heat-sealing property) of wet shell film | | Δ | ○ | ⊚ | ⊚ | ○ | Δ | ○ | ⊚ | ⊚ | ○ | Δ | ○ | ⊚ | ⊚ | ○ |

TABLE 2

| | | Sample No. | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|
| Compounding (part(s) by weight) | Base material | Hydroxypropylated distarch phosphate | | | 20 | | | | | 10 | | | | | 0 | | |
| | | Heat-moisture-treated starch | | | 0 | | | | | 10 | | | | | 20 | | |
| | | Indigestible dextrin | | | 80 | | | | | 80 | | | | | 80 | | |
| | Gelling agent | Locust bean gum | 2 | 4 | 10 | 14 | 18 | 2 | 4 | 10 | 14 | 18 | 2 | 4 | 10 | 14 | 18 |
| | | Xanthane gum | 18 | 16 | 10 | 6 | 2 | 18 | 16 | 10 | 6 | 2 | 18 | 16 | 10 | 6 | 2 |
| | Plasticizer | Glycerin | | | 30 | | | | | 30 | | | | | 30 | | |
| | Water | | | | 200 | | | | | 200 | | | | | 200 | | |
| Evaluation | State 1 (stickiness) of wet shell film | | ○ | ⊚ | ⊚ | ○ | Δ | ○ | ⊚ | ⊚ | ○ | Δ | ○ | ⊚ | ⊚ | ○ | Δ |
| | State 2 (heat-sealing property) of wet shell film | | Δ | ○ | ⊚ | ⊚ | ○ | Δ | ○ | ⊚ | ⊚ | ○ | Δ | ○ | ⊚ | ⊚ | ○ |
| | Appearance of capsule | | | | | | | | | | | | ○ | ⊚ | ⊚ | ○ | Δ |
| | Physical property 1 (adhesiveness) of capsule | | | | | | | | | | | | ○ | ⊚ | ⊚ | ○ | Δ |
| | Physical property 2 (hardness) of capsule | | | | | | | | | | | | Δ | ⊚ | ⊚ | ⊚ | ○ |

TABLE 3

| | | Sample No. | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|---|
| Compounding (part(s) by weight) | Base material | Hydroxypropylated distarch phosphate | | | 50 | | | | | 25 | | | | | 0 | | |
| | | Heat-moisture-treated starch | | | 0 | | | | | 25 | | | | | 50 | | |
| | | Indigestible dextrin | | | 50 | | | | | 50 | | | | | 50 | | |
| | Gelling agent | Locust bean gum | 2 | 4 | 10 | 14 | 18 | 2 | 4 | 10 | 14 | 18 | 2 | 4 | 10 | 14 | 18 |
| | | Xanthane gum | 18 | 16 | 10 | 6 | 2 | 18 | 16 | 10 | 6 | 2 | 18 | 16 | 10 | 6 | 2 |
| | Plasticizer | Glycerin | | | 30 | | | | | 30 | | | | | 30 | | |
| | Water | | | | 200 | | | | | 200 | | | | | 200 | | |
| Evaluation | State 1 (stickiness) of wet shell film | | ○ | ◎ | ◎ | ○ | △ | ○ | ◎ | ◎ | ○ | △ | ○ | ◎ | ◎ | ○ | △ |
| | State 2 (heat-sealing property) of wet shell film | | △ | ○ | ◎ | ◎ | ○ | △ | ○ | ◎ | ◎ | ○ | △ | ○ | ◎ | ◎ | ○ |
| | Appearance of capsule | | | | | | | | | | | | ○ | ◎ | ◎ | ○ | △ |
| | Physical property 1 (adhesiveness) of capsule | | | | | | | | | | | | ○ | ◎ | ◎ | ○ | △ |
| | Physical property 2 (hardness) of capsule | | | | | | | | | | | | △ | ◎ | ◎ | ◎ | ○ |

TABLE 4

| | | Sample No. | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|
| Compounding (part(s) by weight) | Base material | Hydroxypropylated distarch phosphate | | | 70 | | | | | 35 | | | | | 0 | | |
| | | Heat-moisture-treated starch | | | 0 | | | | | 35 | | | | | 70 | | |
| | | Indigestible dextrin | | | 30 | | | | | 30 | | | | | 30 | | |
| | Gelling agent | Locust bean gum | 2 | 4 | 10 | 14 | 18 | 2 | 4 | 10 | 14 | 18 | 2 | 4 | 10 | 14 | 18 |
| | | Xanthane gum | 18 | 16 | 10 | 6 | 2 | 18 | 16 | 10 | 6 | 2 | 18 | 16 | 10 | 6 | 2 |
| | Plasticizer | Glycerin | | | 30 | | | | | 30 | | | | | 30 | | |
| | Water | | | | 200 | | | | | 200 | | | | | 200 | | |
| Evaluation | State 1 (stickiness) of wet shell film | | ○ | ◎ | ◎ | ○ | △ | ○ | ◎ | ◎ | ○ | △ | ○ | ◎ | ◎ | ○ | △ |
| | State 2 (heat-sealing property) of wet shell film | | △ | △ | ○ | ◎ | ○ | △ | △ | ○ | ◎ | ○ | △ | △ | ○ | ◎ | ○ |
| | Appearance of capsule | | | | | | | | | | | | ○ | ◎ | ◎ | ○ | △ |
| | Physical property 1 (adhesiveness) of capsule | | | | | | | | | | | | ○ | ◎ | ◎ | ○ | △ |
| | Physical property 2 (hardness) of capsule | | | | | | | | | | | | △ | ◎ | ◎ | ◎ | ○ |

TABLE 5

| | | Sample No. | 61 | 62 | 63 | 64 | 65 |
|---|---|---|---|---|---|---|---|
| Compounding (part(s) by weight) | Base material | Hydroxypropylated distarch phosphate | | | 0 | | |
| | | Heat-moisture-treated starch | | | 20 | | |
| | | Indigestible dextrin | | | 80 | | |
| | Gelling agent | Locust bean gum | 0.05 | 5 | 10 | 15 | 40 |
| | | Xanthane gum | 0.05 | 5 | 10 | 15 | 40 |
| | Plasticizer | Glycerin | | | 30 | | |
| | Water | | | | 200 | | |
| Evaluation | State 1 (stickiness) of wet shell film | | ○ | ◎ | ◎ | ◎ | ○ |
| | State 2 (heat-sealing property) of wet shell film | | ○ | ◎ | ◎ | ◎ | ○ |
| | Appearance of capsule | | ○ | ◎ | ◎ | ◎ | ○ |
| | Physical property 1 (adhesiveness) of capsule | | ○ | ◎ | ◎ | ◎ | ○ |
| | Physical property 2 (hardness) of capsule | | ○ | ◎ | ◎ | ◎ | ○ |

As shown in Tables 1 to 5 above, it was found that the shell composition of the present invention is useful as a capsule shell and the like, and can become a substituent for a conventional gelatin shell or a conventional plant-derived shell produced using carrageenan.

The invention claimed is:

1. A shell composition formed with:
a plant-derived water-insoluble powder;
a plant-derived water-soluble polymer;
locust bean gum; and
xanthane gum, wherein
the shell composition is a soft capsule shell composition,
a ratio of a weight of the plant-derived water-insoluble powder divided by a weight of the plant-derived water-soluble polymer is in a range equal to or greater than 20/80 and equal to or less than 50/50,
a ratio of a weight of the locust beam gum divided by a weight of the xanthan gum is in a range equal to or greater than 20/80 and equal to or less than 70/30,
a total of the locust bean gum and the xanthan gum is in an amount of 10 to 30 parts by weight relative to 100 parts by weight of a total of the plant-derived water-insoluble powder and the plant-derived water-soluble polymer, and
the plant-derived water-insoluble powder includes starch.

2. The shell composition according to claim 1, wherein the shell composition includes no animal-derived material and no carrageenan.

3. The shell composition according to claim 1, wherein the starch includes at least one of distarch phosphate and heat-moisture-treated starch.

4. The shell composition according to claim 3, wherein the starch includes the distarch phosphate, and the distarch phosphate includes at least one of etherified distarch phosphate and esterified distarch phosphate.

5. The shell composition according to claim 4, wherein the distarch phosphate includes the etherified distarch phosphate, and the etherified distarch phosphate includes hydroxypropyl distarch phosphate.

6. The shell composition according to claim 1, wherein the plant-derived water-soluble polymer includes at least one of a starch decomposition product and polydextrose.

7. A capsule preparation comprising:
a shell composition formed with:
a plant-derived water-insoluble powder;
a plant-derived water-soluble polymer;
locust bean gum; and
xanthane gum; and
an orally-administrable article encapsulated in the shell composition, wherein
the shell composition is a soft capsule shell composition,
a ratio of a weight of the plant-derived water-insoluble powder divided by a weight of the plant-derived water-soluble polymer is in a range equal to or greater than 20/80 and equal to or less than 50/50,
a ratio of a weight of the locust beam gum divided by a weight of the xanthan gum is in a range equal to or greater than 20/80 and equal to or less than 70/30,
a total of the locust bean gum and the xanthan gum is in an amount of 10 to 30 parts by weight relative to 100 parts by weight of a total of the plant-derived water-insoluble powder and the plant-derived water-soluble polymer, and
the plant-derived water-insoluble powder includes starch.

8. The capsule preparation according to claim 7, wherein the orally-administrable article is food.

9. The capsule preparation according to claim 7, wherein the orally-administrable article is a drug.

10. A method for manufacturing a shell composition, comprising:
preparing a shell solution with:
water;
a plant-derived water-insoluble powder;
a plant-derived water-soluble polymer;
locust bean gum; and
xanthane gum; and
gelatinizing the shell solution to obtain the shell composition, the shell composition being a soft capsule shell composition, wherein
a ratio of a weight of the plant-derived water-insoluble powder divided by a weight of the plant-derived water-soluble polymer is in a range equal to or greater than 20/80 and equal to or less than 50/50,
a ratio of a weight of the locust beam gum divided by a weight of the xanthan gum is in a range equal to or greater than 20/80 and equal to or less than 70/30,
a total of the locust bean gum and the xanthan gum is in an amount of 10 to 30 parts by weight relative to 100 parts by weight of a total of the plant-derived water-insoluble powder and the plant-derived water-soluble polymer, and
the plant-derived water-insoluble powder includes starch.

11. The method according to claim 10, wherein the shell solution includes no animal-derived material and no carrageenan.

12. The method according to claim 10, wherein the plant-derived water-soluble polymer includes at least one of a starch decomposition product and polydextrose.

* * * * *